(12) United States Patent
Heo et al.

(10) Patent No.: US 11,690,542 B2
(45) Date of Patent: *Jul. 4, 2023

(54) NON-INVASIVE BIOMETRIC SENSOR BASED ON ORGANIC PHOTODETECTOR

(71) Applicant: Samsung Electronics Co., Ltd., Suwon-si (KR)

(72) Inventors: Chui Joon Heo, Busan (KR); Kyung Bae Park, Hwaseong-si (KR); Takkyun Ro, Hwaseong-si (KR); Kwang Hee Lee, Yongin-si (KR); Dongseon Lee, Suwon-si (KR); Yong Wan Jin, Seoul (KR); Moon Gyu Han, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 58 days.

This patent is subject to a terminal disclaimer.

(21) Appl. No.: 17/005,396

(22) Filed: Aug. 28, 2020

(65) Prior Publication Data

US 2020/0390373 A1 Dec. 17, 2020

Related U.S. Application Data

(63) Continuation of application No. 15/637,628, filed on Jun. 29, 2017, now Pat. No. 10,786,186.

(30) Foreign Application Priority Data

Jun. 30, 2016 (KR) .......................... 10-2016-0082792

(51) Int. Cl.
*A61B 5/1455* (2006.01)
*A61B 5/0295* (2006.01)
(Continued)

(52) U.S. Cl.
CPC .......... *A61B 5/1455* (2013.01); *A61B 5/0295* (2013.01); *A61B 5/14532* (2013.01);
(Continued)

(58) Field of Classification Search
CPC . A61B 5/1455; A61B 5/0295; A61B 5/14532; A61B 5/02416; A61B 5/0261; A61B 5/489

See application file for complete search history.

(56) References Cited

U.S. PATENT DOCUMENTS 6,122,042 A 9/2000 Wunderman et al.
7,643,860 B2 1/2010 Gueissaz
(Continued)

FOREIGN PATENT DOCUMENTS

| JP | H11-216131 A | 8/1999 |
|----|--------------|--------|
| JP | 2000-258343 A | 9/2000 |
| KR | 10-2016-0007889 A | 1/2016 |

OTHER PUBLICATIONS

Jyoti Yadav et al., "Near-infrared LED based Non-invasive Blood Glucose Sensor", 2014, International conference on signal processing and integrated networks (SPIN), pp. 591-594.
(Continued)

*Primary Examiner* — Georgia Y Epps
*Assistant Examiner* — Don J Williams
(74) *Attorney, Agent, or Firm* — Harness, Dickey & Pierce, P.L.C.

(57) ABSTRACT

Disclosed is a non-invasive biometric sensor including a light source, an organic photodetector, and a detector. The light source is configured to irradiate light in a desired (and/or alternatively predetermined) wavelength range to a body part. The organic photodetector is configured to sense the light in the desired (and/or alternatively predetermined) wavelength range in response to the light in the desired (Continued)

(and/or alternatively predetermined) range being transmitted through the body part. The detector is configured to determine biomedical information of the body part based on an amount of the light sensed by the organic photodetector.

20 Claims, 14 Drawing Sheets

(51) Int. Cl.
*A61B 5/145* (2006.01)
*A61B 5/00* (2006.01)
*A61B 5/024* (2006.01)
*A61B 5/026* (2006.01)

(52) U.S. Cl.
CPC ......... *A61B 5/0261* (2013.01); *A61B 5/02416* (2013.01); *A61B 5/489* (2013.01)

(56) References Cited

U.S. PATENT DOCUMENTS

| | | |
|---|---|---|
| 7,787,924 B2 | 8/2010 | Acosta et al. |
| 10,786,186 B2 * | 9/2020 | Heo ..................... A61B 5/1455 |
| 2016/0087012 A1 | 3/2016 | Lee et al. |
| 2017/0135586 A1 | 5/2017 | Jeon et al. |
| 2017/0135616 A1 | 5/2017 | Sato |

OTHER PUBLICATIONS

Jyoti Yadav et al., "Comparative Study of Different Measurement Sites using NIR Based Non-invasive Glucose Measurement System", Procedia Computer Science 70 (2015) 469-475.

Ilana Harman-Boehm et al., "Noninvasive Glucose Monitoring: A Novel Approach", Journal of Diabetes Science and Technology, 3, Mar. 2, 2009.

Korean Office Action dated Mar. 30, 2023 of the corresponding KR application No. 10-2016-0082792 and English translation thereof.

* cited by examiner

NON-INVASIVE BIOMETRIC SENSOR BASED ON ORGANIC PHOTODETECTOR

RELATED APPLICATIONS

This application is a continuation of U.S. Ser. No. 15/637,628, filed on Jun. 29, 2017, which claims priority under 35 U.S.C. § 119 to Korean Patent Application No. 10-2016-0082792 filed in the Korean Intellectual Property Office on Jun. 30, 2016, the entire contents of each of which are incorporated herein by reference.

BACKGROUND

1. Field

A non-invasive biometric sensor based on an organic photodetector is disclosed.

2. Description of Related Art

Recently, the population of adults with chronic diseases, such as diabetes, has increased. Adults with diabetes may use invasive biometric sensors for continuous monitoring.

SUMMARY

Inventive concepts relate to a non-invasive biometric sensor having a high photoelectric conversion efficiency with no light loss.

Inventive concepts also relate to a flexible non-invasive biometric sensor, which is bendable, stretchable, easy to carry.

According to some example embodiments, the non-invasive biometric sensor may include a light source, an organic photodetector, and a detector. The light source may be configured to irradiate light in a desired (and/or alternatively predetermined) wavelength range to a body part. The organic photodetector may be configured to sense light in the desired (and/or alternatively predetermined) wavelength range in response to the light in the desired (and/or alternatively predetermined) wavelength range being transmitted through the body part. The detector is configured to determine biomedical information of the body part based on an amount of the light sensed by the organic photodetector.

In some example embodiments, the light source and the organic photodetector may face each other such that the body part may be positioned between the light source and the organic photodetector. An angle between the light source and the organic photodetector may be about 180°.

In some example embodiments, the biomedical information may be a blood glucose concentration and the desired wavelength range may be a range of about 750 nm to about 1100 nm, the biomedical information may be a heartbeat rate and the desired wavelength range may be about 680 nm to 750 nm, and the biomedical information may be a vein image in the desired wavelength range may be a range of about 770 nm to about 950 nm.

In some example embodiments, the organic photodetector may have a thickness of greater than 0 μm and less than or equal to about 10 μm.

In some example embodiments, a distance between the light source and the organic photodetector may be greater than 0 mm and less than or equal to about 10 mm.

In some example embodiments, the organic photodetector may include an organic photoelectric conversion layer between a first electrode and a second electrode. The organic photoelectric conversion layer may be configured to selectively receive light in the desired wavelength range. The first electrode may be a transparent electrode. The first electrode may be configured to contact the body part.

In some example embodiments, the light source may be a flexible LED.

In some example embodiments, the light source may include at least a first light source and a second light source that may be configured to emit light having different wavelengths from each other and may be arranged in a matrix of n×m (n, m each may be an integer of greater than or equal to about 1).

In some example embodiments, the organic photodetector may include at least a first organic photodetector and a second organic photodetector that may be configured to selectively receive lights having different wavelengths from each other and may be arranged in a matrix of n×m (n, m each may be integer of greater than or equal to about 1).

In some example embodiments, the biomedical information may include at least two of a blood glucose concentration, a heartbeat rate, or a vein image. The desired wavelength range may include at least two of the first wavelength range of about 750 nm to about 1100 nm, a second wavelength range of about 680 nm to about 750 nm, and a third wavelength range of about 770 nm to about 950 nm. The desired wavelength range may include the first wavelength range if the biomedical information includes the blood glucose concentration. The desired wavelength range may include the second wavelength range if the biomedical information includes the heartbeat rate. The desired wavelength range may include the third wavelength range if the biomedical information includes the vein image.

In some example embodiments, the body part may be an ear lobe or a finger acupoint Hapkok. The light source may be configured to irradiate the light in the desired wavelength range to the body part if the body part is the ear lobe or the finger acupoint Hapkok. The organic photo detector may be configured to sense the light in the desired wavelength range in response to the light in the desired wavelength range being transmitted through the body part if the body part is the ear lobe or the finger acupoint Hapkok. The detector may be configured to determine the biomedical information of the body part based on the amount of the light sensed by the organic photodetector if the body part is the ear lobe or the finger acupoint Hapkok.

In some example embodiments, the light source and the organic photodetector may be formed separately from the detector. The light source and the organic photodetector may be configured to transmit information corresponding to a light amount of near infrared radiation to the detector in either a wire way or a wireless way.

According to some example embodiments, the non-invasive blood glucose sensor may include a light source configured to irradiate a near infrared ray light to a body part, an organic photodetector configured to sense the near infrared ray light transmitted through the body part, and a detector configured to determine the blood glucose concentration based on a light amount of the near infrared ray light sensed by the organic photodetector.

In some example embodiments, a thickness of the organic photodetector may be greater than 0 nm and less than or equal to about 10 μm.

In some example embodiments, a distance between the light source and the organic photodetector may be greater than 0 mm and less than or equal to about 10 mm.

In some example embodiments, the organic photodetector may include an organic photoelectric conversion layer between a first electrode and a second electrode. The organic photoelectric conversion layer may be configured to receive the near infrared ray light. The first electrode may be a transparent electrode. The first electrode may be configured to contact the body part.

In some example embodiments, the organic photoelectric conversion layer may include PEDOT/PSS or PTT/PCBM.

In some example embodiments, the light source may be a flexible LED.

In some example embodiments, the body part may be an ear lobe or a finger acupoint Hapkok. The light source may be configured to irradiate the near infrared ray light to the body part if the body part is the ear lobe or the finger acupoint Hapkok. The organic photo detector may be configured to sense the near infrared ray light in response to the near infrared ray light in being transmitted through the body part if the body part is the ear lobe or the finger acupoint Hapkok. The detector may be configured to determine the blood glucose concentration of the body part based on the amount of the near infrared ray light sensed by the organic photodetector if the body part is the ear lobe or the finger acupoint Hapkok.

In some example embodiments, the light source and the organic photodetector may be separate from the detector. The light source and the organic photodetector may be configured to transmit information corresponding to a light amount of the near infrared ray light to the detector in either a wire way or a wireless way.

According to some example embodiments, a non-invasive biometric sensor may include a light source, an organic photodetector, and a detector. The light source may be configured to irradiate near infrared ray light to a body part. The organic photodetector may face the light source and may be spaced apart therefrom. The organic photodetector may be configured to generate an output signal in response to the light source transmitting a portion of the near infrared ray light through the body part. The detector may be configured to determine biomedical information based on the output signal from the organic photodetector.

In some example embodiments, the organic photodetector may not include a color filter layer. The organic photo detector may include an organic photoelectric conversion layer.

In some example embodiments, the detector may be configured to determine a glucose concentration in the body part as the biomedical information based on a reference correlation between the output signal and the glucose concentration.

In some example embodiments, the light source may be a flexible LED.

In some example embodiments, the light source may include a first light source and a second light source that may be configured to emit light having different wavelengths from each other in the near infrared range. The organic photodetector may include at least a first organic photodetector and a second organic photodetector, which may be configured to selectively receive light having different wavelengths from each other and may be arranged in an organic photodetector the matrix of n×m (n, m each may be integer of greater than or equal to about 1).

As the photodetector includes the organic photodetector, the light loss may be reduced, and the photoelectric conversion efficiency may be enhanced. The conventional inorganic photodetector needs a color filter for receiving light in the desired wavelength region, causing the light loss. In addition, basically, the conventional inorganic photodetector is difficult to distinguish a minute difference of biomass due to the low photoelectric conversion efficiency. On the other hand, the organic photodetector may selectively sense light in a desirable wavelength region, so that it has merits of less light loss and higher photoelectric conversion efficiency.

In addition, the conventional inorganic photodetector is formed on a semiconductor substrate, so it is difficult to provide a flexible (flexible, bendable, stretchable) shape; on the other hand, the organic photodetector may be formed in a state of being bendable or stretchable, so the portability and the versatility are improved.

DETAILED DESCRIPTION

Figure 1:
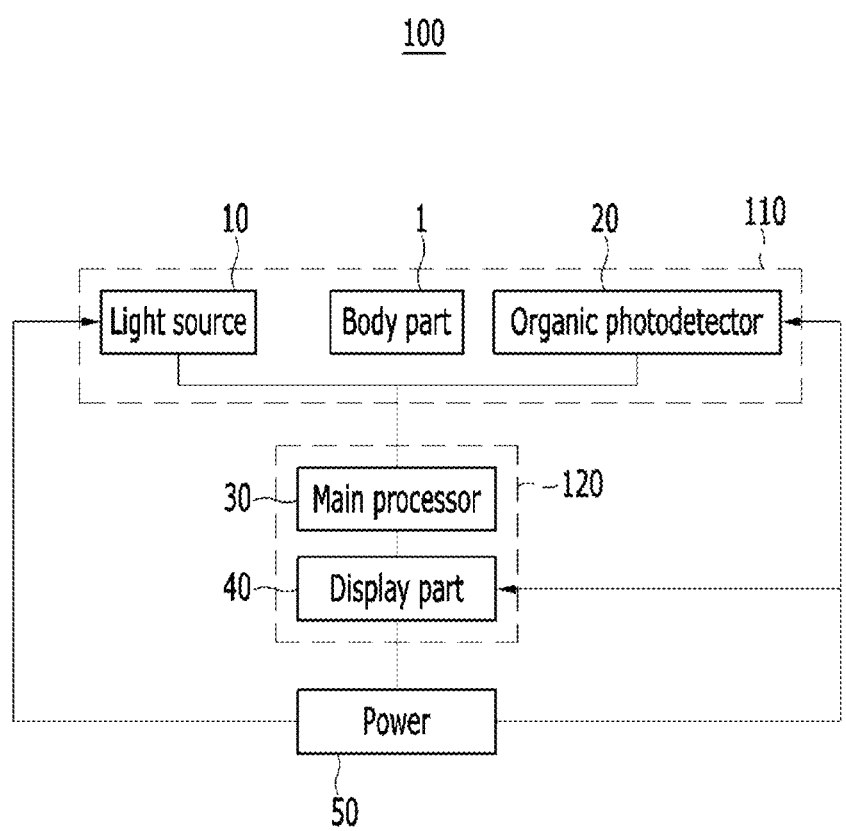
FIG. 1 is a schematic view of a non-invasive blood glucose sensor according to some example embodiments.

Example embodiments will hereinafter be described in detail, and may be easily performed by those who have common knowledge in the related art. However, inventive concepts may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Hereinafter, a non-invasive blood glucose sensor according to some example embodiments is described with reference to the drawings.

FIG. 1 is a schematic view of a non-invasive blood glucose sensor 100 according to some example embodiments.

Referring to FIG. 1, the non-invasive blood glucose sensor 100 according to some example embodiments includes a near infrared ray light source 10 and an organic photodetector 20 disposed so a body part 1 is between the near infrared light source 10 and the organic photodetector 20, a main processor 30, a display part 40, and a power part 50.

The near infrared ray light source 10 and the organic photodetector 20 may provide a measurement part 110, and the main processor 30 and the display part 40 may provide a detector 120. In addition, the measurement part 110, which is formed in separate from the detector 120, may send a measurement signal to the detector 120 in either wire or wireless method. In the wire method, the measurement signal may be directly transmitted through an electrode of the organic photodetector; but in the wireless method, the measurement part 110 may further include a wireless signal sender for transmitting the measurement signal of the organic photodetector, and the detector 120 may further include a wireless signal receiver.

When the detector 120 is formed separately as above, the measurement part 110 may be easily formed in a down-size and a thin-film, so as to provide a variety of shapes such as a clip shape or a patch shape.

The near infrared ray (NIR) light source 10 uses light having a wavelength of 750-2500 nm, which may penetrate a tissue in a low energy radiation. As the specific agent is not required for the measurement, it may be repeatedly analyzed in a very low cost. The detector 120 may be used to determine biomedical information and/or measure biometric signals (e.g., concentration of a chemical such as glucose, other metrics such as heart rate etc.). For example, measuring light having a wavelength of about 750 nm to about 1100 nm enables measurement of glucose in a depth of several nm or less from a skin tissue. Glucose absorbs a peak of 939 nm, 970 nm, 1197 nm in a high overtone region, a peak of 1408 nm, 1536 nm, 1688 nm, 1925 nm in a first overtone region, and a peak of 2100 nm, 2261 nm, 2326 nm in a combination region. Thus, the near infrared ray light source 10 may include a light source emitting light in a NIR wavelength of about 940 nm. Even though glucose shows a small absorption peak at 940 nm compared to the first overtone region and the combination region, the light may penetrate in a desirable depth since it does not occur the phenomenon like an optical signal attenuation caused by other components such as water. Meanwhile, as a light source, a LED may be better than a laser. This is because the laser is expensive and has a larger volume when being formed as a light source and requires a large cooling device; on the other hand, the LED has a small volume and is cheap and consumes a relatively small voltage and does not need a cooling device, Also, compared to a laser, the LED may damages tissue less.

In addition, in order to enhance portability and versatility, it may use a flexible LED in which LED is mounted on a soft flexible printed circuit (FPC) board.

The photodetector 20 may be an organic photodetector and thus may be applied to the various body parts. The organic photodetector may have a merit in portability and versatility as it is bendable or stretchable.

The main processor 30 may control the near infrared ray light radiation of the near infrared ray light source 10 and may also improve the results by amplifying the received signal from the organic photodetector 20 and by removing interference signals caused by other biological chromophores (e.g., protein, lipid, water, etc.). The main processor 30 may be a hardware processor such as central processing unit (CPU), a multi-processor, a distributed processing system, an application specific integrated circuit (ASIC), and/or a suitable hardware processing unit. The main processor 30 may include a memory (not shown). The memory may be a nonvolatile memory, such as a flash memory, a phase-change random access memory (PRAM), a magneto-resistive RAM (MRAM), a resistive RAM (Re-RAM), or a ferro-electric RAM (FRAM), or a volatile memory, such as a static RAM (SRAM), a dynamic RAM (DRAM), or a synchronous DRAM (SDRAM). The main processor 30 may execute instructions stored in the memory to perform some or all of the operations described herein.

The display part 40 displays the results of the signal processor 30 in convenient for a user. The display part 40 may be a generally-used display or a flexible display considering portability and versatility.

The power part 50 may provide power to each of constituent elements 10, 20, 30, and 40 for the non-invasive blood glucose sensor 100. The power part may include a power source (e.g., battery) and a power circuit.

Figure 2:
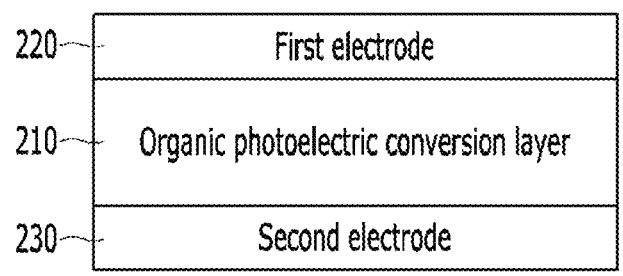
FIG. 2 is a schematic view of an organic photodetector.

The organic photodetector 20 includes an organic photoelectric conversion layer 210 capable of absorbing (and/or configured to absorb) a near infrared ray in a selected wavelength band and a first electrode 220 and a second electrode 230 formed on both surfaces of the organic photoelectric conversion layer 210 as shown in FIG. 2. It is more effective to condense light which has scattered by a measurement subject 1 that at least one electrode of the first electrode 220 and the second electrode 230, which is contacted with the measurement subject, is a transparent electrode. The organic photodetector 20 may be formed without a color filter layer.

The transparent electrode may be made of a transparent conductor such as indium tin oxide (ITO), indium zinc oxide (IZO) or a metal thin film having a thin thickness of several nanometers to several ten nanometers (e.g., 3 nm to 100 nm and/or 5 nm to 80 nm) or a metal oxide-doped metal thin film having a single layer or a multilayer having a thin thickness of several nanometers to several ten nanometers e.g., 3 nm to 100 nm and/or 5 nm to 80 nm). However, example embodiments are not limited thereto.

The organic photoelectric conversion layer 210 may absorb a near infrared ray in a selected wavelength and transmit other light as it is except the absorbed near infrared ray. Thereby, an additional near infrared ray filter is not required, so that it has a merit of less light loss compared to the conventional inorganic photodiode. As the organic photoelectric conversion layer 210 absorbs a near infrared ray in the selected wavelength band, the signal generated by other materials besides glucose in blood may be reduced (and/or minimized).

An organic photoelectric conversion layer 210 may include PEDOT/PSS (doped poly (2, 4-ethylenedioxythiophene)/poly(styrene sulfonic acid)) or PTT/PCBM (Polythieno[3,4-b]thiophene/6 and 6-phenyl C61-butyric acid methyl ester) being capable of absorbing (and/or configured to absorb) a near infrared ray.

Figure 3:
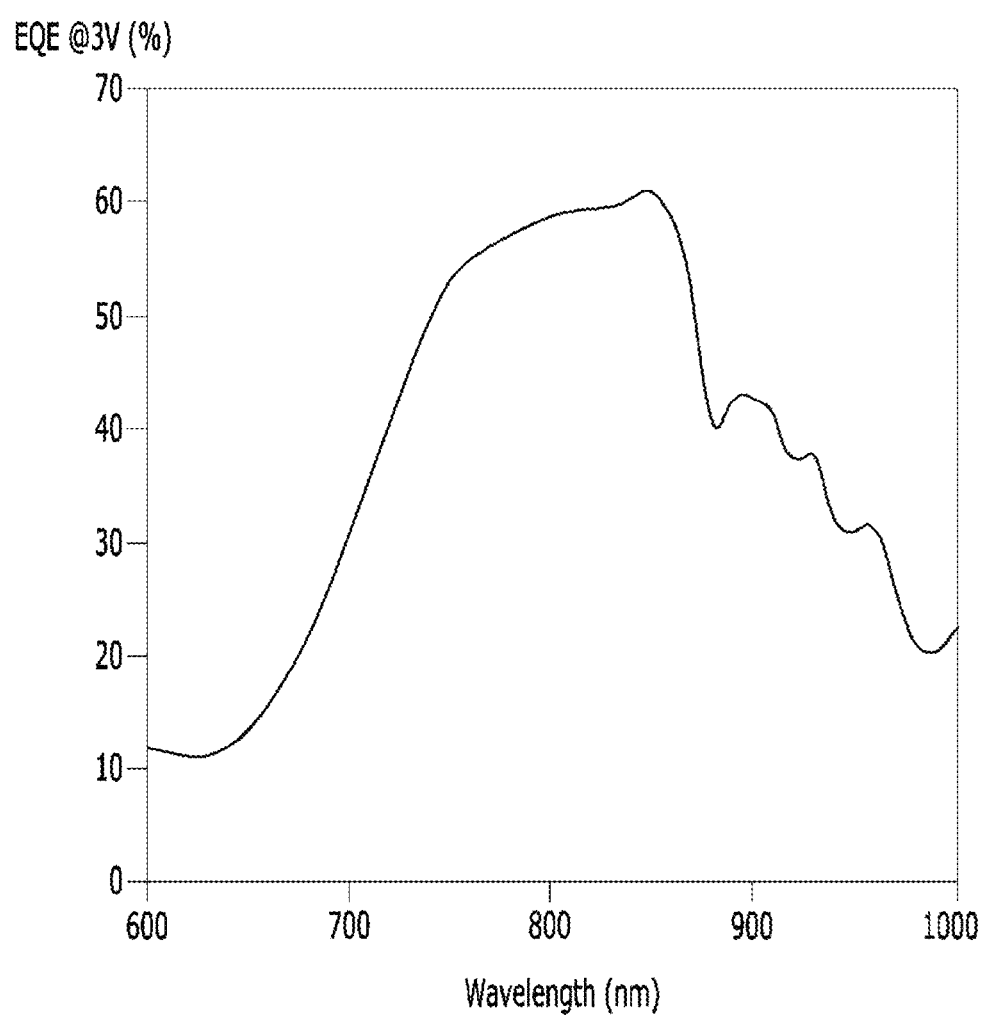
FIG. 3 is a graph showing a photoelectric conversion efficiency of a near infrared ray light-receiving organic photoelectric conversion layer.

In addition, as shown in FIG. 3, the organic photoelectric conversion layer 210 shows a high photoelectric conversion efficiency for light in a wavelength band of about 700-1100 nm, so the signal detecting efficiency may be increased (and/or maximized). Particularly, the photoelectric conversion efficiency is greater than or equal to about 40% in a wavelength band of about 750-930 nm.

As the organic photodetector 20 is bendable or stretchable, it may have a merit of portability and versatility. The thickness of the organic photodetector 20 may be less than or equal to about 10 μm, so that it may be remarkably effective to down-size the non-invasive blood glucose sensor 100.

Figure 4:
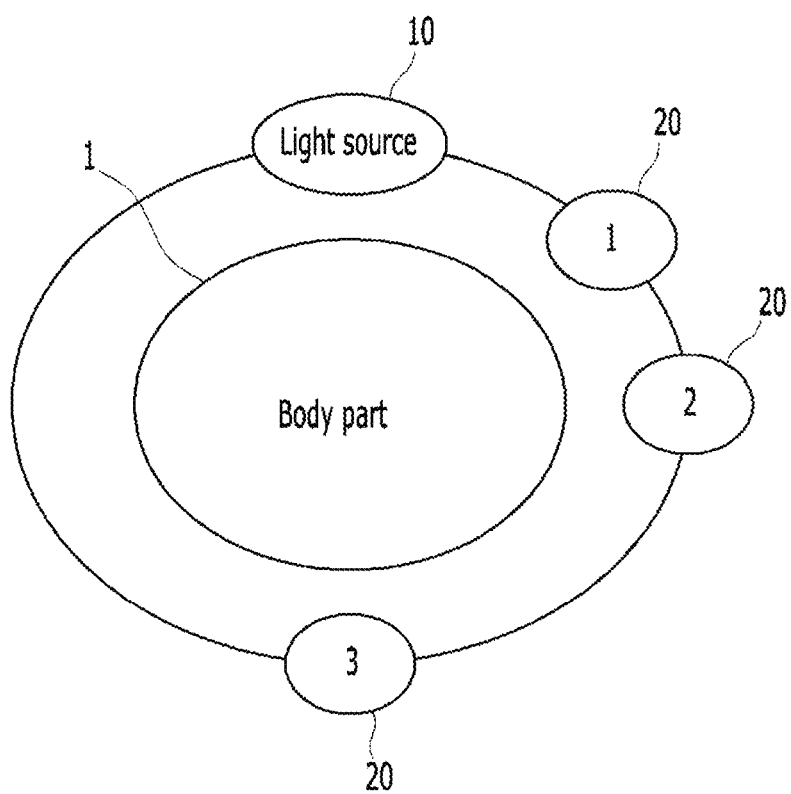
FIG. 4 is a schematic view showing an angle of between a near infrared ray light source and an organic photodetector based on a body part.

As shown in FIG. 4, based on a body part 1, the near infrared ray light source 10 and the organic photodetector 20 may form an angle of 45° (1), 90° (2), or 180° (3). Among them, in a case that the near infrared ray light source 10 and the organic photodetector 20 are disposed on opposite sides of the body part and face each other (180°, 3), more light scattered by blood glucose may reach the organic photodetector 20, so that it may be more accurately measured.

Figure 5A:
FIGS. 5A and 5B are images showing an ear lobe and a finger acupoint Hapkok which may be applied with a non-invasive blood glucose sensor.
Figure 5B:
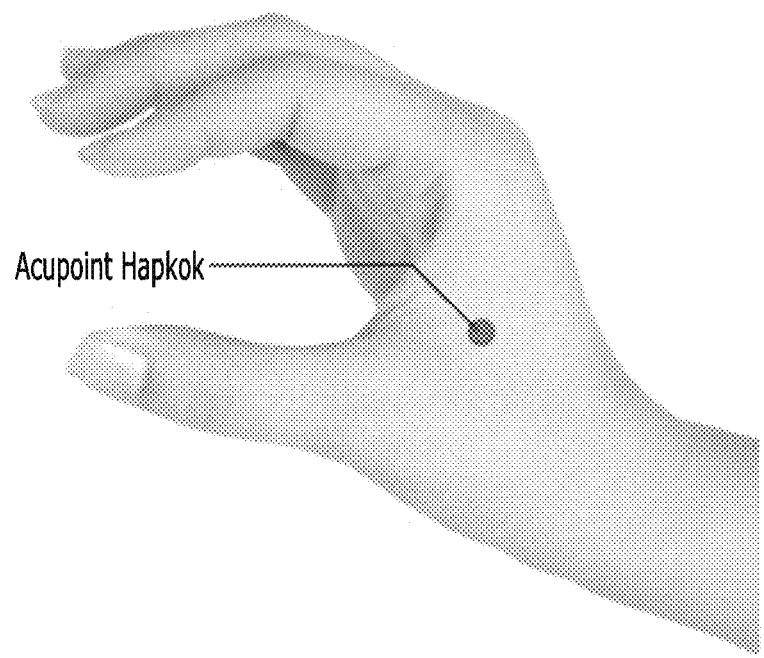

As in above, the body part enabling the near infrared ray light source 10 and the organic photodetector 20 to be disposed in an opposite side to each other may be an ear lobe of FIG. 5A, but the region the majority part is composed of only dermis including epidermis and blood vessels with no bones, such as a finger acupoint Hapkok of FIG. 5B, may be also preferable. The ear lobe and finger acupoint Hapkok are examples of the body part 1, but inventive concepts are not limited thereto.

Figure 6:
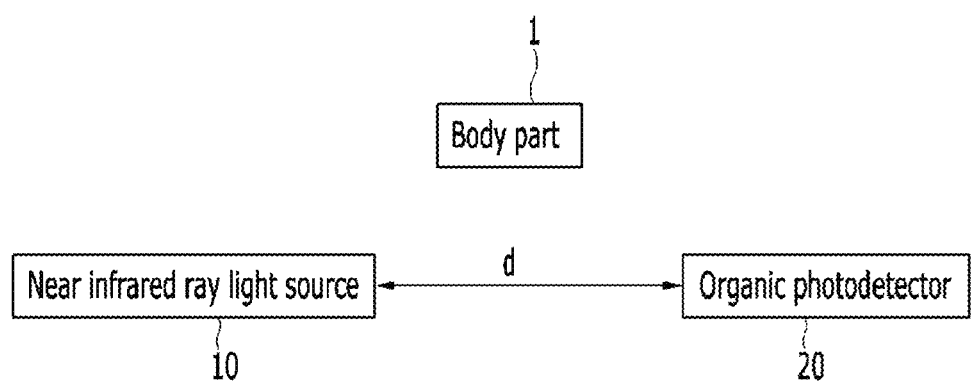
FIG. 6 is a schematic view for illustrating a distance between a near infrared ray light source and an organic photodetector in a non-invasive blood glucose sensor according to some example embodiments.

FIG. 6 is a schematic view illustrating a distance (d) between the near infrared ray light source 10 and the organic photodetector 20 in a non-invasive blood glucose sensor 100 according to some example embodiments.

As illustrated in FIGS. 5A and 5B, the ear lobe or the finger acupoint Hapkok where are appropriate for the measurement has a thickness of less than or equal to about 10 mm, so the distance (d) between the near infrared ray light source 10 and the organic photodetector 20 in the non-invasive blood glucose sensor 100 may be greater than 0 mm and also less than or equal to about 10 mm. The distance (d) may be greater than a thickness of the ear lobe or the finger acupoint Hapkok.

In order to measure a glucose level in a blood vessel, the near infrared ray irradiated from the near infrared ray light source 10 may pass through epidermis, reach the dermis, and run into glucose in the blood vessel; consequently, the near infrared ray may be scattered and pass again through the epidermis and then focus to the organic photodetector 20.

Figure 7:
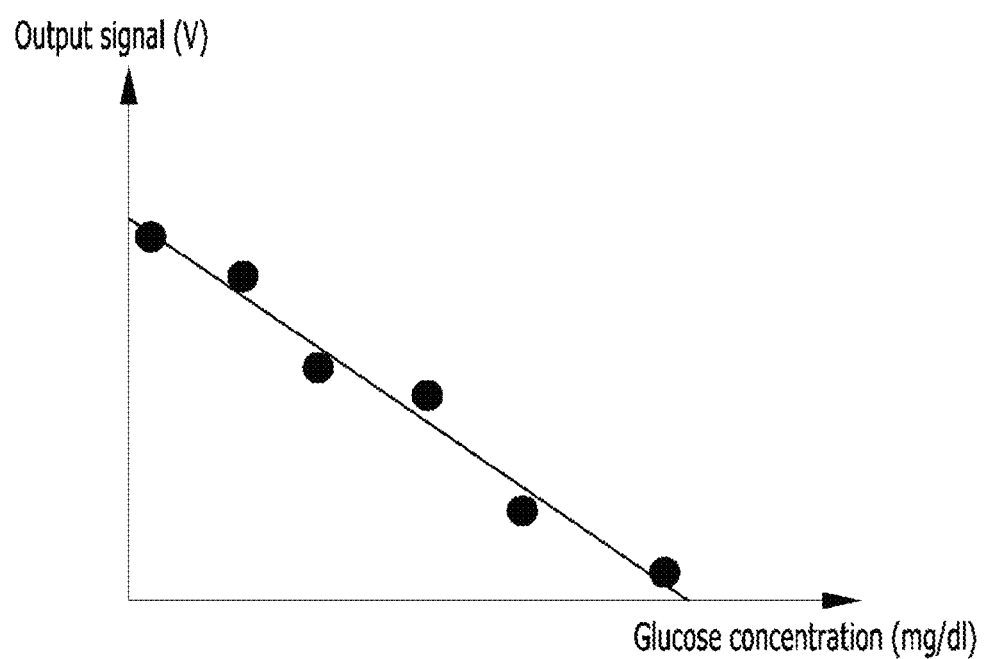
FIG. 7 is a graph showing a correlation between a glucose concentration and an output signal of an organic photodetector.

In this case, as shown in FIG. 7, it shows a correlation that the output signal of the organic photodetector 20 is getting decreased as much as the glucose concentration is higher. Accordingly, by applying the correlation shown in FIG. 7, the glucose concentration of body part 1 may be quantified.

Referring to FIGS. 1 to 7, the non-invasive blood glucose sensor according to some example embodiments enhances the measurement accuracy by using an organic photodetector including an organic photoelectric conversion layer significantly selective to a near infrared ray, and the light loss may be reduced (and/or minimized) as the additional near infrared ray filter is not required, so that the minute blood glucose difference may be analyzed.

On the other hand, in the case of the non-invasive blood glucose sensor obtained by using the near infrared ray LED and the inorganic photodiode suggested by the literature in 2014 (Near-infrared LED based Non-Invasive Blood Glucose Sensor, 2014 International conference on signal processing and integrated networks (SPIN)), it is difficult to completely separate a photo reaction signal caused by other materials in a body, and the additional large signal analysis system (spectrophotometer, etc.) for improving the problem is needed, causing the difficulty to be commercialized, and the additional near infrared ray filter is required, causing the considerable light loss.

Furthermore, the sensor obtained by the method disclosed in the literature is difficult and/or impossible to be downsized, and the measurement accuracy may be questioned due to the calibration with a tiny light amount.

Figure 8:
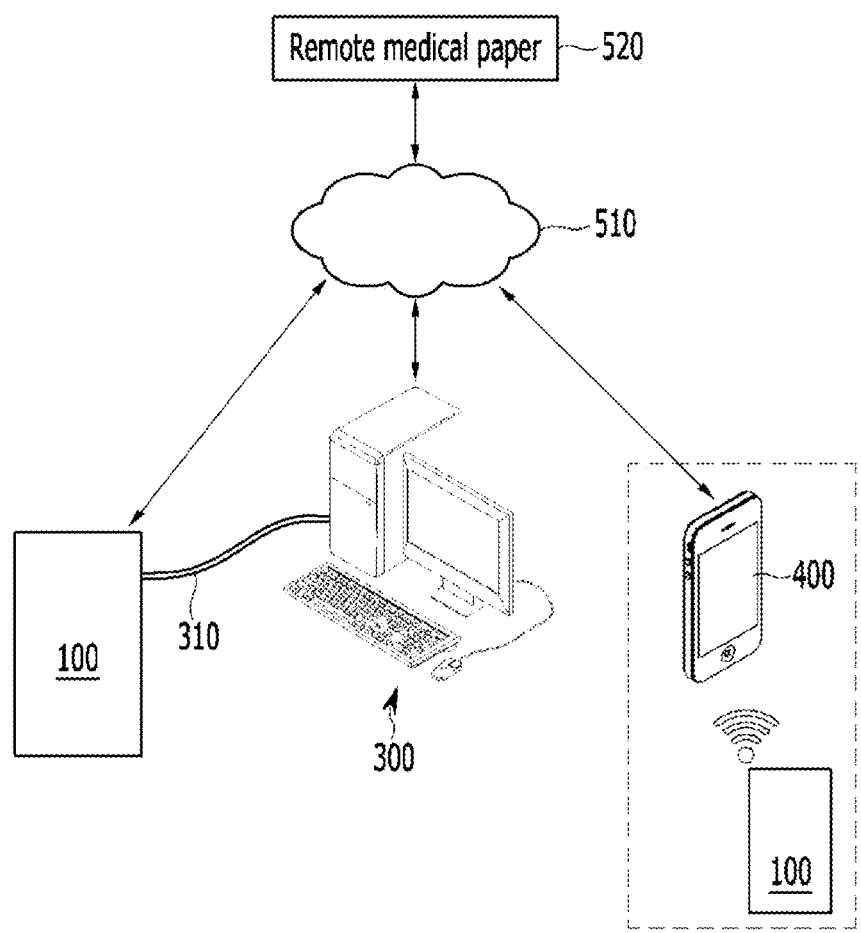
FIG. 8 is a schematic view showing a transmission of information measured by a non-invasive blood glucose sensor according to some example embodiments.

FIG. 8 shows a transmission of information measured by a non-invasive blood glucose sensor 100 according to some example embodiments.

The information measured by the non-invasive blood glucose sensor 100 is transmitted to a computer 300 or a personal portable terminal 400 through USB 310 over wires and then managed for a history. In addition, the information measured by the non-invasive blood glucose sensor 100 may be delivered to a computer 300 or a personal portable terminal 400 wirelessly through, for example, Bluetooth, WiFi, infrared ray (IR), and the like.

Meanwhile, the computer 300 or the personal portable terminal 400 may be connected to a remote medical paper 520 through a communication network 510, enabling a telemedicine and telemanagement. Needless to say, the non-invasive blood glucose sensor 100 may be directly connected to the remote medical paper 520 through a communication network 510.

As above, the non-invasive blood glucose sensor 100 may further include a USB connector, a wireless transceiver or the like in order to transmit/receive the information with a computer 300, a portable terminal 400 and a remote medical paper 520.

Figure 9:
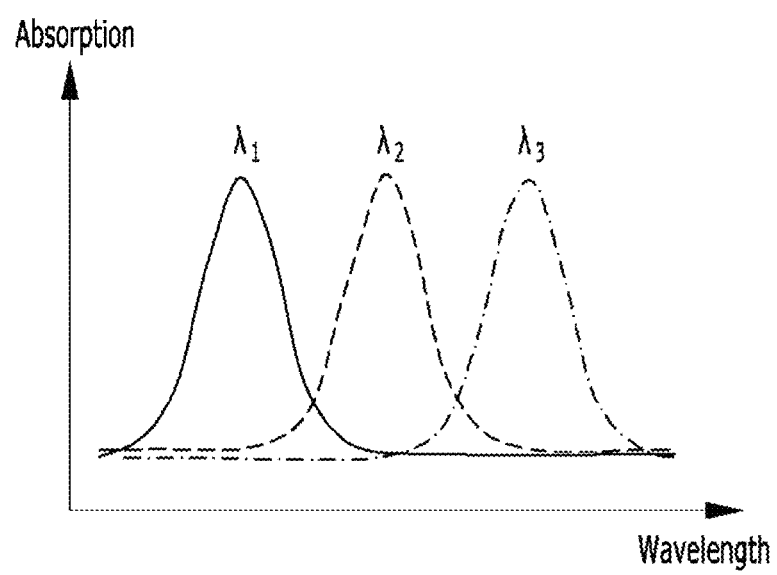
FIG. 9 is a graph showing that a wavelength range of a light source and a wavelength of light selectively absorbed by an organic photoelectric conversion layer may be selected.

As shown in FIG. 9, when the wavelength range ($\lambda 1$, $\lambda 2$, or $\lambda 3$) of the light irradiated from the light source 10 and the wavelength of light where the organic photoelectric conversion layer 210 of the organic photodetector 20 selectively absorbs the same are modified into a wavelength range ($\lambda 1$, $\lambda 2$, or $\lambda 3$) of the light source irradiated from the light source in the non-invasive blood glucose sensor 100, the various non-invasive biometric sensors for measuring a variety of bio materials may be obtained.

For example, the organic photodetector 20 may measure heartbeat when the wavelength range of the light irradiated from the light source is about 680 nm to about 750 nm ($\lambda 1$), and the organic photoelectric conversion layer 210 selectively senses light of about 680 nm to about 750 nm.

In addition, it may measure a vein image when the wavelength range of the light irradiated from the light source is about 770 nm to about 950 nm ($\lambda 2$), and the organic photoelectric conversion layer 210 selectively senses light of about 770 nm to about 950 nm.

Figure 10:
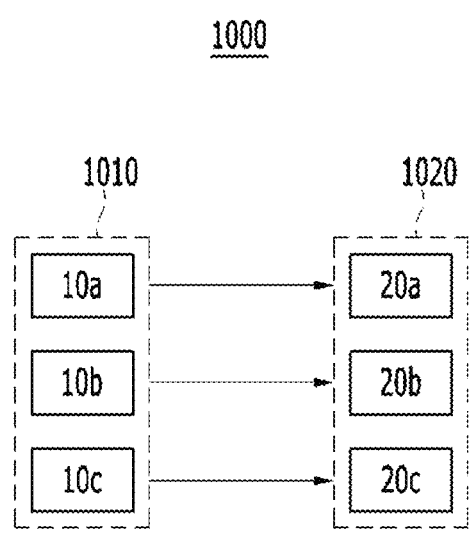
FIG. 10 is a schematic view of a biometric sensor capable of simultaneously measuring a plurality of biometric signals.

FIG. 10 is a schematic view of a biometric sensor 1000 capable of simultaneously measuring a plurality of biometric signals.

The light source 1010 includes light sources 10a, 10b, and 10c having different wavelengths ($\lambda 1$, $\lambda 2$, and $\lambda 3$), and the organic photodetector 1020 includes a plurality of organic photodetectors 20a, 20b, and 20c sensing different wavelengths ($\lambda 1$, $\lambda 2$, and $\lambda 3$), so the organic photodetector 1020 may simultaneously measure a plurality of biometric signals such as blood glucose, heartbeat, a vein image and the like.

FIG. 10 shows the case that the light sources 10a, 10b, and 10c and the organic photodetectors 20a, 20b, and 20c are formed in 1×3, as an example, but it may be modified into n×m, where n and m independently are positive integers.

Figure 11A:
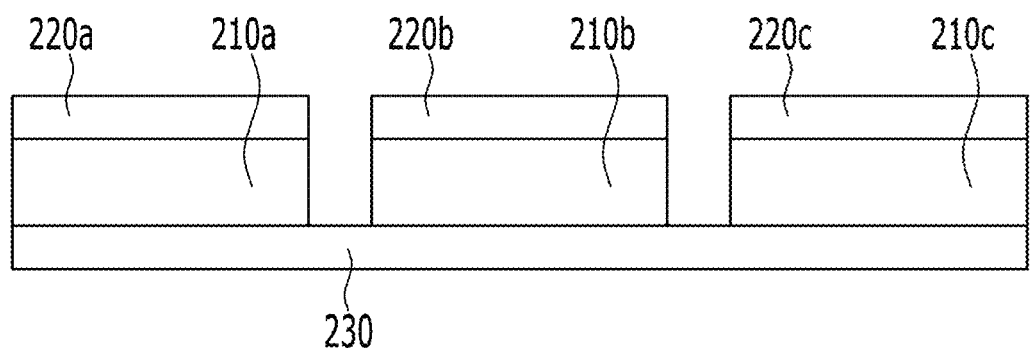
FIGS. 11A and 11B are cross-sectional views of organic photodetectors of biometric sensors capable of measuring (and/or configured to measure) a plurality of biometric signals.
Figure 11B:
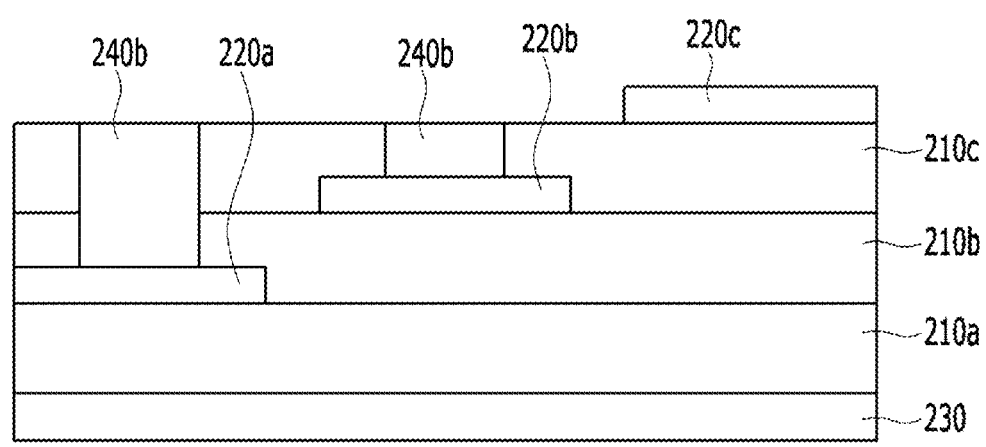

FIGS. 11A and 11B each show cross-sectional views of organic photodetectors 20 of biometric sensors capable of measuring (and/or configured to measure) a plurality of biometric signals. The organic photodetectors 20 in FIGS. 11A and/or 11B may be formed without a color filter layer.

FIG. 11A shows a case that the different organic photoelectric conversion layers 210a, 210b, and 210c selectively absorbing lights having different wavelengths (λ1, λ2, and λ3) from each other and first electrodes 220a, 220b, and 220c are patterned on the positions corresponding to each of light sources 10a, 10b, and 10c, respectively.

FIG. 11B shows a case that the different organic photoelectric conversion layers 210a, 210b, and 210c selectively absorbing lights having different wavelengths (λ1, λ2, and λ3) are sequentially stacked; and first electrodes 220a, 220b, and 220c, which have each been patterned for discharging charge gathered by the selectively absorbed light onto the organic photoelectric conversion layer 210a, 210b, and 210c, are formed on the organic photoelectric conversion layers 210a, 210b, and 210c; and the first electrode 220a on the lowermost organic photoelectric conversion layer 210a and the first electrode 220b on the middle organic photoelectric conversion layer 210b discharge charge through via 240a and 240b, respectively.

Figure 12:
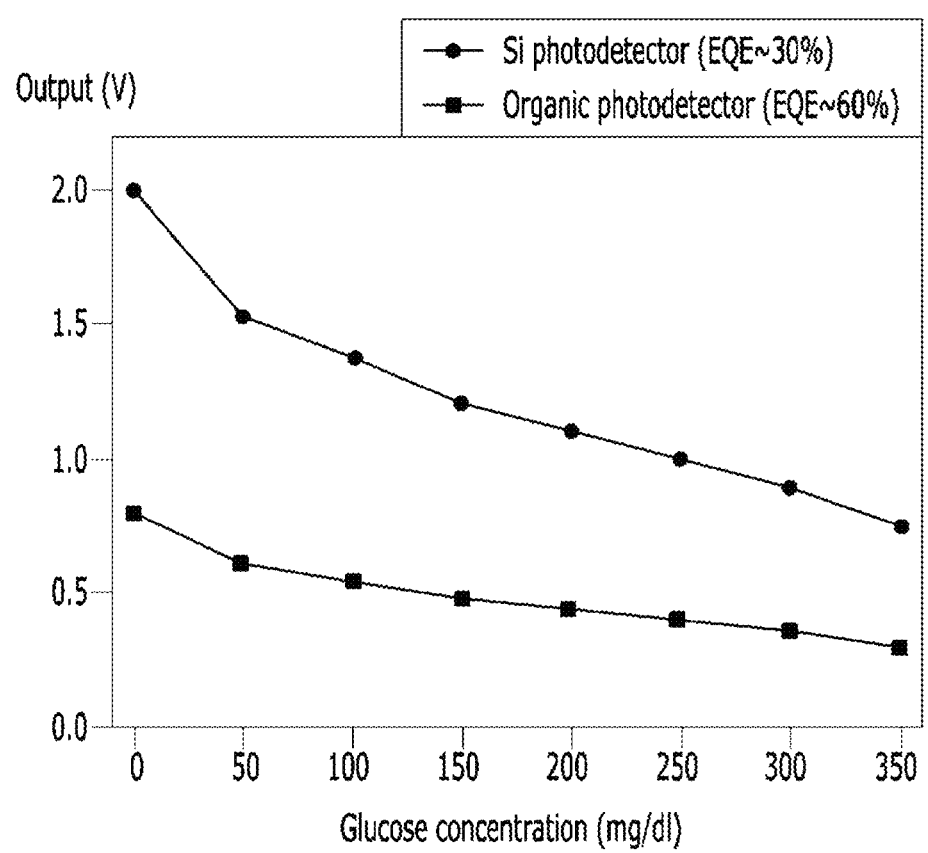
FIG. 12 is a graph showing a measurement sensitivity of a non-invasive blood glucose sensor which includes the conventional Si photodiode having a photoelectric conversion efficiency of about 30% and a non-invasive blood glucose sensor which includes a near infrared ray organic photodetector having a photoelectric conversion efficiency of at maximum about 60%.

FIG. 12 is a graph showing a relationship between the glucose concentration measured by a non-invasive blood glucose sensor which includes the conventional Si photodiode having a photoelectric conversion efficiency of maximum about 30% and the output (V) thereof; and a relationship between the glucose concentration measured by a non-invasive blood glucose sensor which includes a near infrared ray organic photodetector having a photoelectric conversion efficiency of maximum about 60% and the output (V) thereof. It is understood that the entire measurement sensitivity is enhanced by employing the organic photodetector.

Although non-invasive biometric sensors according to some example embodiments have been described for measuring a blood glucose concentration, inventive concepts are not limited thereto. One of ordinary skill in the art would appreciate that non-invasive biometric sensors according to some example embodiments may be used to detect other chemicals in the blood.

It should be understood that example embodiments described herein should be considered in a descriptive sense only and not for purposes of limitation. Descriptions of features or aspects within each device or method according to example embodiments should typically be considered as available for other similar features or aspects in other devices or methods according to example embodiments. While some example embodiments have been particularly shown and described, it will be understood by one of ordinary skill in the art that variations in form and detail may be made therein without departing from the spirit and scope of the claims.

What is claimed is:

1. A non-invasive biometric sensor comprising:
a light source configured to irradiate light in a desired wavelength range to a body part;
an organic photodetector configured to sense the light in the desired wavelength range in response to the light in the desired wavelength range being transmitted through the body part; and
a detector configured to determine biomedical information of the body part based on an amount of the light sensed by the organic photodetector by using a correlation,
wherein the biomedical information includes a blood glucose concentration, and according to the correlation, the amount of the light sensed by the organic photodetector is inversely proportional to the blood glucose concentration.

2. The non-invasive biometric sensor of claim 1, wherein the light source and the organic photodetector face each other such that the body part may be positioned between the light source and the organic photodetector, and
an angle between the light source and the organic photodetector is about 45° or about 90°.

3. The non-invasive biometric sensor of claim 1, wherein the desired wavelength range is a range of about 750 nm to about 1100 nm.

4. The non-invasive biometric sensor of claim 1, wherein a thickness of the organic photodetector is greater than 0 μm and less than or equal to about 10 μm.

5. The non-invasive biometric sensor of claim 1, wherein a distance between the light source and the organic photodetector is greater than 0 mm and less than or equal to about 10 mm.

6. The non-invasive biometric sensor of claim 1, wherein
the organic photodetector includes an organic photoelectric conversion layer between a first electrode and a second electrode,
the organic photoelectric conversion layer is configured to selectively receive light in the desired wavelength range,
the first electrode is a transparent electrode, and
the first electrode is configured to contact the body part.

7. The non-invasive biometric sensor of claim 1, wherein the light source is a flexible LED.

8. The non-invasive biometric sensor of claim 1, wherein
the light source includes at least a first light source and a second light source that are configured to emit light having different wavelengths from each other and are arranged in a light source matrix of n×m,
n and m are each integers that are greater than or equal to 1, and
the organic photodetector includes at least a first organic photodetector and a second organic photodetector that are configured to selectively receive light having different wavelengths from each other and are arranged in an organic photodetector matrix of n×m.

9. The non-invasive biometric sensor of claim 8, wherein
the biomedical information includes the blood glucose concentration and at least one of a heartbeat rate or a vein image,
the desired wavelength range includes a first wavelength range of about 750 nm to about 1100 nm and at least one of a second wavelength range of about 680 nm to about 750 nm and a third wavelength range of about 770 nm to about 950 nm,
the desired wavelength range includes the second wavelength range if the biomedical information includes the heartbeat rate, and
the desired wavelength range includes the third wavelength range if the biomedical information includes the vein image.

10. The non-invasive biometric sensor of claim 1, wherein
the light source is configured to irradiate the light in the desired wavelength range to the body part if the body part is an ear lobe or a finger acupoint Hapkuk,
the organic photodetector configured to sense the light in the desired wavelength range in response to the light in the desired wavelength range being transmitted through the body part if the body part is the ear lobe or the finger acupoint Hapkuk, and the detector is configured to determine the biomedical information of the body part based on the amount of the light sensed by the organic photodetector if the body part is the ear lobe or the finger acupoint Hapkuk.

11. The non-invasive biometric sensor of claim 1, wherein the light source and the organic photodetector are separate from the detector, and the light source and the organic photodetector are configured to transmit information corresponding to a light amount of near infrared radiation to the detector in either a wire way or a wireless way.

12. A non-invasive blood glucose sensor comprising:
a light source configured to irradiate near infrared ray light to a body part for measuring a blood glucose concentration;
an organic photodetector configured to sense the near infrared ray light transmitted through the body part; and
a detector configured to determine the blood glucose concentration based on a light amount of the near infrared ray light sensed by the organic photodetector by using a correlation,
wherein according to the correlation, the light amount of the near infrared ray light sensed by the organic photodetector is inversely proportional to the blood glucose concentration.

13. The non-invasive blood glucose sensor of claim 12, wherein a thickness of the organic photodetector is greater than 0 μm and less than or equal to about 10 μm.

14. The non-invasive blood glucose sensor of claim 12, wherein a distance between the light source and the organic photodetector is greater than 0 mm and less than or equal to about 10 mm.

15. The non-invasive blood glucose sensor of claim 12, wherein
the organic photodetector includes an organic photoelectric conversion layer between a first electrode and a second electrode,
the organic photoelectric conversion layer is configured to receive the near infrared ray light,
the first electrode is a transparent electrode, and
the first electrode is configured to contact the body part.

16. The non-invasive blood glucose sensor of claim 15, wherein the organic photoelectric conversion layer includes PEDOT/PSS or PTT/PCBM.

17. The non-invasive blood glucose sensor of claim 12, wherein the light source is a flexible LED.

18. The non-invasive blood glucose sensor of claim 12, wherein
the light source is configured to irradiate the near infrared ray light to the body part if the body part is an ear lobe or a finger acupoint Hapkuk,
the organic photodetector configured to sense the near infrared ray light in response to the near infrared ray light being transmitted through the body part if the body part is the ear lobe or the finger acupoint Hapkuk, and
the detector is configured to determine the blood glucose concentration of the body part based on the light amount of the near infrared ray light sensed by the organic photodetector if the body part is the ear lobe or the finger acupoint Hapkuk.

19. The non-invasive blood glucose sensor of claim 12, wherein
the light source and the organic photodetector are separate from the detector, and
the light source and the organic photodetector are configured to transmit information corresponding to the light amount of the near infrared ray light to the detector in either a wire way or a wireless way.

20. A non-invasive biometric sensor comprising:
a light source configured to irradiate near infrared ray light to a body part;
an organic photodetector facing the light source and spaced apart therefrom, the organic photodetector being configured to generate an output signal in response to the light source transmitting a portion of the near infrared ray light through the body part; and
a detector configured to determine biomedical information based on the output signal from the organic photodetector by using a correlation,
wherein the biomedical information is a blood glucose concentration, and according to the correlation, the output signal from the organic photodetector is inversely proportional to the blood glucose concentration.

* * * * *

UNITED STATES PATENT AND TRADEMARK OFFICE
CERTIFICATE OF CORRECTION

| | |
|---|---|
| PATENT NO. | : 11,690,542 B2 |
| APPLICATION NO. | : 17/005396 |
| DATED | : July 4, 2023 |
| INVENTOR(S) | : Chul Joon Heo et al. |

It is certified that error appears in the above-identified patent and that said Letters Patent is hereby corrected as shown below:

On the Title Page

Item (72) insert:
-- (72) Inventors: Chul Joon Heo --

Signed and Sealed this
Sixteenth Day of April, 2024

Katherine Kelly Vidal
*Director of the United States Patent and Trademark Office*